US012352689B2

(12) United States Patent  
Pelliccia

(10) Patent No.: US 12,352,689 B2  
(45) Date of Patent: Jul. 8, 2025

(54) DETECTING PLANT PRODUCT PROPERTIES

(71) Applicant: RUBENS IP PTY LTD, Rowville (AU)

(72) Inventor: Daniele Pelliccia, Rowville (AU)

(73) Assignee: RUBENS IP PTY LTD, Rowville (AU)

( * ) Notice: Subject to any disclaimer, the term of this patent is extended or adjusted under 35 U.S.C. 154(b) by 203 days.

(21) Appl. No.: 18/011,992

(22) PCT Filed: Jun. 24, 2021

(86) PCT No.: PCT/AU2021/050660  
§ 371 (c)(1),  
(2) Date: Dec. 21, 2022

(87) PCT Pub. No.: WO2021/258148  
PCT Pub. Date: Dec. 30, 2021

(65) Prior Publication Data  
US 2023/0236117 A1 Jul. 27, 2023

(30) Foreign Application Priority Data  
Jun. 24, 2020 (AU) ................................ 2020902117

(51) Int. Cl.  
*G01N 21/33* (2006.01)  
*G01J 3/02* (2006.01)  
(Continued)

(52) U.S. Cl.  
CPC ............ *G01N 21/33* (2013.01); *G01J 3/0224* (2013.01); *G01J 3/0291* (2013.01); *G01J 3/4406* (2013.01);  
(Continued)

(58) Field of Classification Search  
CPC .... G01J 3/2823; G01J 3/10; G01J 2003/2826; G01J 3/02; G01J 3/0272; G01J 3/28;  
(Continued)

(56) References Cited

U.S. PATENT DOCUMENTS 6,052,187 A 4/2000 Krishnan  
11,156,501 B1 * 10/2021 Zhang ........................ G01J 3/10  
(Continued)

FOREIGN PATENT DOCUMENTS

CN 106950196 7/2017  
CN 108732133 11/2018  
(Continued)

OTHER PUBLICATIONS

PCT International Search Report and Written Opinion of PCT Application No. PCT/AU2021/050660, mailed Aug. 3, 2021 (11 pages).

*Primary Examiner* — Michael P Stafira  
(74) *Attorney, Agent, or Firm* — Esplin & Associates, PC

(57) ABSTRACT

A method for detecting at least one property of a plant product, the method including: directing source light including ultraviolet (UV) light at UV wavelengths and polarized visible and/or near-infrared (VIS/NIR) light at VIS/NIR wavelengths onto a region of the plant product; blocking the polarized VIS/NIR light of the source light, and blocking polarized specular reflection from the region of the plant product, from being transmitted to a visible and/or near-infrared (VIS/NIR) spectrometer; and transmitting a portion of emitted light caused by fluorescence and/or diffuse reflection from the region of the plant product to the visible and/or near-infrared (VIS/NIR) spectrometer.

20 Claims, 8 Drawing Sheets

(51) Int. Cl.
*G01J 3/44* (2006.01)
*G01N 21/35* (2014.01)
*G01N 21/47* (2006.01)
G01J 3/10 (2006.01)

(52) U.S. Cl.
CPC ......... *G01N 21/35* (2013.01); *G01N 21/4738* (2013.01); *G01J 2003/102* (2013.01); *G01N 2021/4792* (2013.01)

(58) Field of Classification Search
CPC .......... G01J 3/0205; G01J 3/42; G01J 3/2803; G01J 3/0291; G01J 3/36; G01J 3/0256; G01J 3/0224; G01J 3/0264; G01J 3/44; G01J 2003/1213; G01J 2003/104; G01J 3/12; G01J 3/0218; G01J 3/32; G01J 3/0216; G01J 3/453; G01J 3/0208; G01J 3/0289; G01J 3/108; G01J 3/021; G01J 3/0297; G01J 3/14; G01J 3/1838; G01J 3/0229; G01J 5/10; G01J 2003/123; G01J 3/027; G01J 2003/1239; G01J 3/0275; G01J 3/0294; G01J 2003/1208; G01J 2003/1282; G01J 3/0232; G01J 3/0262; G01J 3/4406; G01J 2003/1221; G01J 2003/1243; G01J 2003/284; G01J 3/0283; G01J 2001/4242; G01J 2003/2806; G01J 2003/4334; G01J 3/457; G01J 3/433; G01J 1/0266; G01J 2003/102; G01J 3/0286; G01J 3/4412; G01J 3/51; G01J 2003/4332; G01J 3/18; G01J 3/427; G01J 3/50; G01J 1/0411; G01J 3/1256; G01J 3/46; G01J 3/502; G01J 3/508; G01J 5/04; G01J 5/0816; G01J 5/0831; G01J 5/20; G01J 5/59; G01J 2011/005; G01J 3/0237; G01J 3/08; G01J 3/2846; G01J 3/45; G01J 3/4531; G01J 3/513; G01J 4/04; G01J 1/0242; G01J 2003/064; G01J 2003/1226; G01J 2003/283; G01J 3/0245; G01J 3/0248; G01J 3/0259; G01J 3/06; G01J 3/1895; G01J 1/0204; G01J 1/0219; G01J 1/0233; G01J 1/0247; G01J 1/0271; G01J 1/0414; G01J 1/4228; G01J 2003/1217; G01J 2003/2866; G01J 3/0202; G01J 3/0221; G01J 3/0278; G01J 3/26; G01J 3/447; G01J 5/0014; G01J 5/0846; G01J 5/0896; G01J 5/80; G01J 2003/106; G01J 2003/1269; G01J 2003/2833; G01J 2003/2836; G01J 2003/425; G01J 3/0227; G01J 3/0243; G01J 3/0254; G01J 3/04; G01J 3/4535; G01J 3/501; G01J 5/027; G01N 21/31; G01N 21/359; G01N 21/255; G01N 21/65; G01N 2201/0221; G01N 21/3563; G01N 21/85; G01N 33/53; G01N 21/35; G01N 2201/129; G01N 2333/525; G01N 2333/545; G01N 33/6869; G01N 33/442; G01N 33/6854; G01N 33/68; G01N 21/4738; G01N 33/02; G01N 21/21; G01N 21/33; G01N 21/645; G01N 2201/062; G01N 33/0098; G01N 33/74; G01N 21/658; G01N 33/15; G01N 33/6863; G01N 2021/3137; G01N 21/3504; G01N 21/39; G01N 2021/1793; G01N 33/4833; G01N 33/6872; G01N 21/88; G01N 2201/08; G01N 2201/12; G01N 21/64; G01N 33/582; G01N 2021/3595; G01N 2021/399; G01N 2201/061; G01N 33/025; G01N 33/49; G01N 21/25; G01N 2021/656; G01N 2201/1293; G01N 2021/8411; G01N 21/49; G01N 2201/06113; G01N 2201/06146; G01N 2800/24; G01N 31/10; G01N 33/533; G01N 33/542; G01N 21/51; G01N 2201/1296; G01N 2800/7028; G01N 33/6857; G01N 21/274; G01N 21/9508; G01N 2333/54; G01N 33/56966; G01N 21/47; G01N 33/54346; G01N 33/6812; G01N 2021/8466; G01N 21/00; G01N 21/27; G01N 2333/515; G01N 2333/705; G01N 33/0075; G01N 21/3103; G01N 2201/0627; G01N 2333/4709; G01N 2333/48; G01N 2333/5443; G01N 2333/7155; G01N 33/245; G01N 33/246; G01N 33/553; G01N 33/6848; G01N 33/88; G01N 2021/3513; G01N 21/55; G01N 21/6456; G01N 21/94; G01N 33/54373; G01N 33/92; G01N 1/2202; G01N 2001/2223; G01N 21/474; G01N 2333/195; G01N 2405/00; G01N 2405/04; G01N 2405/08; G01N 2570/00; G01N 27/624; G01N 2800/26; G01N 3/00; G01N 30/724; G01N 33/487; G01N 33/48735; G01N 33/6851; G01N 9/00; G01N 2021/3155; G01N 2021/317; G01N 21/01; G01N 21/554; G01N 21/8806; G01N 27/623; G01N 33/56983; G01N 2021/3144; G01N 2021/4769; G01N 21/29; G01N 21/3577; G01N 21/9501; G01N 2201/127; G01N 33/6845; G01N 2021/6417; G01N 2021/6491; G01N 2021/8592; G01N 21/23; G01N 21/4795; G01N 21/6428; G01N 21/643; G01N 21/648; G01N 21/8851; G01N 2333/47; G01N 33/54313; G01N 15/1429; G01N 15/1436; G01N 15/1459; G01N 15/1468; G01N 2015/0026; G01N 2015/1006; G01N 2021/0118; G01N 2021/4742; G01N 2021/4792; G01N 21/05; G01N 21/314; G01N 21/53; G01N 2201/0625; G01N 2201/0691; G01N 2201/121; G01N 2469/20; G01N 33/587; G01N 33/6896; G01N 2021/1734; G01N 2021/216; G01N 2021/6419; G01N 21/211; G01N 21/61; G01N 21/6486; G01N 2201/0636; G01N 27/44721; G01N 2800/2814; G01N 33/00; G01N 33/12; G01N 33/1826; G01N 33/505; G01N 33/54333; G01N 33/54353; G01N 33/56911; G01N 33/56972; G01N 33/58; G01N 35/0098; G01N 2021/1738; G01N 2021/479; G01N 2021/6423; G01N 21/253; G01N 21/3581; G01N 21/76; G01N 21/82; G01N 2201/0612; G01N 2201/0634; G01N 2201/068; G01N 2500/04; G01N 33/532; G01N 33/574; G01N 33/60; G01N 1/32; G01N 17/002; G01N 17/004; G01N 2015/03; G01N 2021/054; G01N 2021/335; G01N 2021/4747; G01N 2021/635; G01N 2021/6421; G01N 2021/6432; G01N 2021/6441; G01N 21/41; G01N 21/6408; G01N 21/6489; G01N 21/75; G01N 21/763; G01N 21/84; G01N 2201/0214; G01N 2201/105; G01N 23/223; G01N 30/02; G01N 33/0081; G01N 33/44; G01N 33/5308; G01N 33/57415; G01N 33/585; G01N 33/86; G01N 15/0205; G01N 2021/6439; G01N 2021/6476; G01N 21/3151; G01N 21/532; G01N 21/552; G01N 21/71; G01N 21/783; G01N 21/95; G01N 2201/0216; G01N 2201/0697; G01N 2223/417; G01N 2333/00; G01N 2333/62; G01N 33/24; G01N 33/483; G01N 33/52; G01N 33/531; G01N 33/54393; G01N 1/2247; G01N 11/04; G01N 15/082; G01N 15/1434; G01N 2021/0112; G01N 2021/217; G01N 2021/3174; G01N 2021/3531; G01N 2021/394; G01N 2021/655; G01N 2021/845; G01N 2021/8829; G01N 2021/8848; G01N 2035/0094; G01N 21/3554; G01N 21/45; G01N 21/718; G01N 21/774; G01N 21/8901; G01N 21/8903; G01N 21/9072; G01N 21/9081; G01N 21/93; G01N 2201/021; G01N 2201/06193; G01N 2201/0638; G01N 2201/067; G01N 23/2273; G01N 2333/165; G01N 2333/70596; G01N 2333/726; G01N 2333/96411; G01N 24/08; G01N 2469/10; G01N 25/147; G01N 25/72; G01N 2800/56; G01N 2800/60; G01N 30/7206; G01N 33/0096; G01N 33/14; G01N 33/493; G01N 33/5014; G01N 33/5023; G01N 33/5061; G01N 33/54306; G01N 33/54366; G01N 33/566; G01N 33/569; G01N 33/57426; G01N 33/6842; G01N 33/82; G01N 35/0092; G01N 1/38; G01N 1/405; G01N 11/00; G01N 15/00; G01N 15/1433; G01N 2015/0046; G01N 2015/1486; G01N 2021/0325; G01N 2021/0389; G01N 2021/1736; G01N 2021/174; G01N 2021/1765; G01N 2021/1782; G01N 2021/258; G01N 2021/3133; G01N 2021/3196; G01N 2021/4764; G01N 2021/653; G01N 2021/869; G01N 2021/8816; G01N 2021/8825; G01N 2021/8835; G01N 2021/8845; G01N 2021/8883; G01N 2021/945; G01N 2035/00158; G01N 21/251; G01N 21/3586; G01N 21/4788; G01N 21/553; G01N 21/59; G01N 21/636; G01N 21/6458; G01N 21/66; G01N 21/7703; G01N 21/8422; G01N 21/89; G01N 21/8914; G01N 21/896; G01N 21/9027; G01N 21/95623; G01N 22/00; G01N 2201/0675; G01N 2333/04; G01N 2333/70503; G01N 2333/7051; G01N 2333/70539; G01N 2333/90216; G01N 2458/40; G01N 2500/00; G01N 2500/10; G01N 27/129; G01N 27/622; G01N 2800/36; G01N 2800/50; G01N 31/223; G01N 33/0027; G01N 33/0034; G01N 33/10; G01N 33/146; G01N 33/1893; G01N 33/28; G01N 33/343; G01N 33/5005; G01N 33/5008; G01N 33/5011; G01N 33/5088; G01N 33/5091; G01N 33/5302; G01N 33/5432; G01N 33/54326; G01N 33/54386; G01N 33/56977; G01N 33/57419; G01N 33/57484; G01N 33/57492; G01N 33/64; G01N 33/66; G01N 33/689; G01N 35/00009; G01N 35/00029; G01N 2035/00326; G01N 33/5097; G01N 35/00; G01N 35/1065; G01N 33/6893; G01N 2035/00495; G01N 35/0099; G01N 1/286; G01N 35/026; G01N 35/10; G01N 27/62; G01N 2035/00148; G01N 35/00871; G01N 2035/00366; G01N 35/1072; G01N 35/04; G01N 30/72; G01N 1/28; G01N 2035/0449; G01N 33/50; G01N 35/00069; G01N 2035/00237; G01N 2035/00306; G01N 2015/016; G01N 2035/00138; G01N 2035/00356; G01N 2035/00425; G01N 2035/0486; G01N 2035/0491; G01N 2201/024; G01N 2201/04; G01N 2333/4353; G01N 35/1009; G01N 35/1011; G01N 2015/012; G01N 2035/00435; G01N 2035/00633; G01N 2035/0474; G01N 2035/0493; G01N 2035/0494; G01N 2035/1051; G01N 2333/43526; G01N 33/62; G01N 33/6827; G01N 33/80; G01N 35/00623; G01N 2800/042; G01N 35/1079; G01N 2035/00881; G01N 2223/076; G01N 30/06; G01N 1/4022; G01N 2001/2866; G01N 33/0001; G01N 33/573; G01N 33/18; G01N 2001/4033; G01N 2800/044; G01N 2800/323; G01N 33/5038; G01N 33/6881; G01N 33/6887; G01N 3/08; G01N 33/241; G01N 1/14; G01N 2015/1021; G01N 33/543; G01N 1/24; G01N 2035/1076; G01N 21/78; G01N 3/12; G01N 3/40; G01N 33/48707; G01N 1/08; G01N 33/56961; G01N 1/44; G01N 1/34; G01N 1/40; G01N 13/04; G01N 2223/304; G01N 2458/15; G01N 33/48; G01N 33/5304; G01N 33/57434; G01N 5/025; G01N 2333/8135; G01N 1/02; G01N 1/4077; G01N 2035/0406; G01N 2035/0453; G01N 2035/0465; G01N 2201/0833; G01N 35/00603; G01N 5/02; G01N 1/22; G01N 1/2273; G01N 1/26; G01N 2001/021; G01N 2001/1427; G01N 2035/00277; G01N 2333/33; G01N 2333/90241; G01N 30/88; G01N 33/0036; G01N 33/0057; G01N 2001/382; G01N 2035/103; G01N 2201/0692; G01N 2201/084; G01N 2223/33; G01N 2333/32; G01N 2333/38; G01N 2333/952; G01N 27/44743; G01N 31/12; G01N 33/5082; G01N 33/5306; G01N 33/84; G01N 33/948; G01N 1/2813; G01N 15/0211; G01N 2015/0038; G01N 21/73; G01N 27/44756; G01N 27/626; G01N 30/14; G01N 30/0011; G01N 33/1866; G01N 33/491; G01N 33/5058; G01N 33/5094; G01N 2001/4061; G01N 2030/025; G01N 2030/067; G01N 21/07; G01N 2223/616; G01N 2333/9015; G01N 27/02; G01N 27/44708; G01N 2800/06; G01N 30/7233; G01N 33/561; G01N 35/02; G01N 15/14; G01N 15/147; G01N 2001/1031; G01N 2001/2893; G01N 2001/4083; G01N 2001/4088; G01N 2015/0222; G01N 2021/3572; G01N 2030/062; G01N 2030/8827; G01N 2030/8868; G01N 2035/1048; G01N 21/278; G01N 21/68; G01N 2201/0846; G01N 2201/1241; G01N 27/221; G01N 2800/347; G01N 31/22; G01N 33/04; G01N 33/1813; G01N 33/54388; G01N 33/583; G01N 35/00584; G01N 1/4055; G01N 1/42; G01N 15/01; G01N 2021/0339; G01N 2021/513; G01N 2021/646; G01N 2021/6482; G01N 2027/222; G01N 2035/1035; G01N 2223/1016; G01N 2223/301; G01N 2223/303; G01N 2223/3037; G01N 2223/645; G01N 2223/652; G01N 23/2202; G01N 2333/90209; G01N 27/026; G01N 27/4145; G01N 27/447; G01N 27/72; G01N 30/08; G01N 33/182; G01N 33/559; G01N 1/10; G01N 1/323; G01N 2001/2873; G01N 2021/825; G01N 2030/027; G01N 2035/00811; G01N 21/4133; G01N 2203/0019; G01N 2203/0076; G01N 2458/10; G01N 2800/342; G01N 30/54; G01N 33/243; G01N 33/5047; G01N 35/00732; G01N 35/1097; G01N 1/2294; G01N 1/4005; G01N 1/4044; G01N 15/0227; G01N 2001/1037; G01N 2001/1062; G01N 2001/383; G01N 2001/386; G01N 2011/008; G01N 2015/025; G01N 2015/1497; G01N 2021/3114; G01N 2021/4759; G01N 2021/8427; G01N 2035/00336; G01N 2035/00465; G01N 2035/00475; G01N 2035/00534; G01N 2035/00683; G01N 2035/00772; G01N 2035/0403; G01N 2038/0477; G01N 21/13; G01N 21/72; G01N 21/7746; G01N 21/80; G01N 2223/314; G01N 2291/02458; G01N 2291/02466; G01N 2291/02836; G01N 23/2206; G01N 23/2251; G01N 2333/415; G01N 2333/43573; G01N 2333/9029; G01N 24/082; G01N 25/00; G01N 2560/00; G01N 27/04; G01N 27/22; G01N 27/44717; G01N 27/44726; G01N 27/4473; G01N 27/44791; G01N 2800/00; G01N 2800/52; G01N 29/14; G01N 29/46; G01N 3/02; G01N 30/00; G01N 30/8686; G01N 31/005; G01N 33/1806; G01N 33/222; G01N 33/2847; G01N 33/287; G01N 33/5085; G01N 33/5434; G01N 33/6878; G01N 33/946; G01N 33/9486; G01N 35/08; G01N 9/24; G01N 1/00; G01N 1/04; G01N 1/12; G01N 11/02; G01N 13/02; G01N 15/10; G01N 15/1404; G01N 15/149; G01N 2001/005; G01N 2001/1418; G01N 2015/1472; G01N 2015/1493; G01N 2021/6463; G01N 2021/7759; G01N 2021/8416; G01N 2030/0095; G01N 2030/8405; G01N 2030/884; G01N 2035/00544; G01N 2035/0405; G01N 21/6402; G01N 2333/24; G01N 2333/245; G01N 2333/255; G01N 2333/325; G01N 2333/71; G01N 2333/79; G01N 2333/82; G01N 2333/98; G01N 2400/00; G01N 2430/10; G01N 2430/12; G01N 25/50; G01N 2500/02; G01N 27/3277; G01N 27/44769; G01N 27/745; G01N 2800/02; G01N 2800/245; G01N 30/30; G01N 30/8679; G01N 30/96; G01N 31/221; G01N 31/227; G01N 33/0045; G01N 33/225; G01N 33/38; G01N 33/5064; G01N 33/57438; G01N 33/57473; G01N 33/5767; G01N 33/6803; G01N 33/6824; G01N 33/6875; G01N 33/743; G01N 33/94; G01N 33/9493; G01N 35/1016; G01N 35/1095; G01N 9/36; A01C 1/06; A01C 1/00; A01C 1/08; A01C 21/007; A01C 23/007; A01C 23/042; A01C 21/005; A01C 1/025; A01C 21/00

See application file for complete search history.

(56) References Cited

U.S. PATENT DOCUMENTS

| | | | |
|---|---|---|---|
| 2002/0011567 A1* | 1/2002 | Ozanich | G01J 3/0224 250/326 |
| 2005/0266147 A1 | 12/2005 | Yao | |
| 2008/0101657 A1 | 5/2008 | Durkin | |
| 2010/0111369 A1* | 5/2010 | Lussier | G01N 21/6486 356/417 |
| 2017/0131200 A1* | 5/2017 | Raveh | G01N 21/21 |
| 2018/0172510 A1* | 6/2018 | Rosen | G01J 3/0205 |
| 2018/0184972 A1* | 7/2018 | Carmi | G01J 3/2803 |
| 2019/0174077 A1 | 6/2019 | Mitani | |
| 2019/0216322 A1* | 7/2019 | Anikanov | G01J 3/28 |
| 2019/0219499 A1* | 7/2019 | Gold | G01N 21/359 |
| 2019/0293620 A1 | 9/2019 | Farkas | |
| 2019/0368936 A1* | 12/2019 | Xu | G01J 3/4406 |

FOREIGN PATENT DOCUMENTS

| | | | | |
|---|---|---|---|---|
| CN | 109709103 | | 5/2019 | |
| JP | H05273 | | 10/1993 | |
| WO | 1999056127 | | 11/1999 | |
| WO | WO-2019224043 A1 * | | 11/2019 | A01G 7/00 |

\* cited by examiner

DETECTING PLANT PRODUCT PROPERTIES

TECHNICAL FIELD

The present disclosure generally relates to an apparatus and method for detecting one or more properties of plant products (e.g., fruits and/or vegetables), such as those that are related to plant product maturity and quality (e.g., fruit or vegetable maturity and quality).

BACKGROUND

The quality of a fresh food plant product (e.g., a fruit or vegetable) is typically measured by colour sorting. White illumination can be absorbed at some wavelengths and scattered and/or reflected at other wavelengths, and reflection spectra from fruit can be an indicator of fruit quality. However, visible colour may be a poor indicator of quality and/or ripeness for some fruits/vegetables in some applications, and existing colourimeters and spectrophotometers may be too expensive or inaccurate for some applications, and may not be suitable for using outdoors, e.g., in a field.

Ultraviolet (UV) illumination of a region of a skin or a surface of a plant product, including a piece of fruit or a vegetable (including a leaf or flower), can produce emission of electromagnetic radiation in the visible (VIS) to near-infrared (NIR) range due to electronic excitation and relaxation in one or more pigment molecules present in the skin or surface of the plant product, e.g., chlorophyll, anthocyanins and/or carotenoids (depending on a type and a variety of the plant product). This electromagnetic radiation may be referred to as "pigment fluorescence", e.g., chlorophyll fluorescence. Pigment fluorescence levels in fruit skin can be correlated with a maturity and/or ripening state of the fruit. In addition, chlorophyll fluorescence levels can be used to monitor post-harvest stress disorders in fruit and vegetable products.

Some existing chlorophyll fluorometers use Pulse-Amplitude-Modulation (PAM), relying on a short excitation light sequence and fast detector response to be able to measure extremely fast changes in fluorescence yield in the dark-light transition. As such, chlorophyll fluorometers using PAM techniques use a time-resolved measurement of yield which can be used to evaluate plant physiology parameters. However, detection of plant product properties using a PAM system requires the sample plant product to be dark-adapted, i.e., to be left in the dark for a sufficient amount of time (in the order of 15 minutes) prior to a measurement being made, which can be too long for some applications.

It is desired to address or ameliorate one or more disadvantages or limitations associated with the prior art, or to at least provide a useful alternative.

SUMMARY

The present invention provides a method for detecting at least one property of a plant product, the method including:
 a. directing source light including ultraviolet (UV) light at UV wavelengths and polarized visible and/or near-infrared (VIS/NIR) light at VIS/NIR wavelengths onto a region of the plant product;
 b. blocking the polarized VIS/NIR light of the source light, and polarized specular reflection from the region of the plant product, from being transmitted to a visible and/or near-infrared (VIS/NIR) spectrometer; and
 c. transmitting a portion of emitted light caused by fluorescence and/or diffuse reflection from the region of the plant product to the visible and/or near-infrared (VIS/NIR) spectrometer.

The transmitted portion of the emitted light has an opposite polarization from the polarized VIS/NIR light of the source light. The emitted light is caused by the source light being directed onto the region. The fluorescence and/or diffuse reflection from the region may be the pigment fluorescence and/or natural diffuse reflection from the region of the plant product. The polarized VIS/NIR light and the polarized specular reflection may be blocked by a spectrometer polarizer. The transmitted portion may be transmitted by the spectrometer polarizer. The spectrometer polarizer forms a crossed polarizer to the polarization of the polarized VIS/NIR light of the source light.

The method may include blocking the UV light of the source light and UV specular reflection from the region, and transmitting a portion of the emitted light with VIS/NIR wavelengths. The UV light and the UV specular reflection may be blocked by a UV filter. The transmitted portion may be transmitted by the UV filter.

The UV light may be polarized UV light with the same polarization as the VIS/NIR light. The polarized UV light may be blocked by the spectrometer polarizer.

The method may include acquiring a background spectrum while the source light is not being directed onto the region of the plant product.

The method may include: generating one or more spectra that are indicative of the transmitted portion; storing signals representing the one or more spectra; and transmitting the signals using a communications protocol.

The method may include generating one or more background-free spectra by removing the background spectrum from the one or more spectra indicative of the transmitted portion; storing signals representing the one or more background-free spectra; and transmitting the signals using the communications protocol.

The method may include housing the spectrometer in a protective housing.

The method may include accommodating the plant product in cup, optionally wherein the cup includes a non-linear circumference (i.e., a plurality of folds).

The method may include the cup substantially blocking the spectrometer from background light.

The method may include holding the plant product at a selected distance from spectrometer, optionally using two or more fins.

The present invention provides an apparatus for detecting at least one property of a plant product, the apparatus including:
 a. a light source for directing source light including UV light at UV wavelengths and polarized VIS/NIR light at VIS/NIR wavelengths onto a region of the plant product;
 b. a spectrometer polarizer for blocking the polarized VIS/NIR light of the source light and polarized specular reflection from the region from being transmitted to a visible and/or near-infrared (VIS/NIR) spectrometer, and for transmitting a portion of emitted light caused by fluorescence and/or diffuse reflection from the region; and
 c. the visible-NIR (VIS/NIR) spectrometer for receiving the transmitted portion.

The apparatus may include a UV filter for blocking the UV light of the source light and UV specular reflection from the region, and for transmitting the portion of the emitted light at VIS/IR wavelengths.

The UV light may be polarized UV light with the same polarization as the VIS/NIR light. The spectrometer polarizer blocks the polarized UV light.

The spectrometer may acquire a background spectrum while the light source is not directing source light onto the region of the plant product. The spectrometer may generate one or more spectra that are indicative of the transmitted portion.

The apparatus may include electronics (i.e., electronic components) for reading out and storing signals representing the one or more spectra indicative of the transmitted portion; and for transmitting the signals using a communications protocol.

The electronics may be configured for generating background-free spectra by removing the background spectrum from the one or more spectra indicative of the transmitted portion.

The apparatus may include a protective housing for protecting the spectrometer during use.

The spectrometer may be arranged in substantially the same plane as the light source.

The light source may include at least one UV light source and at least one VIS/NIR light source.

The at least one UV light source and the at least one VIS/NIR light source may include light emitting diodes (LEDs).

The at least one UV light source may include a plurality of UV light sources (elements) arranged in a geometrical arrangement. The geometrical arrangement may be a sequence or a ring.

The at least one VIS/NIR light source may include a plurality of VIS/NIR light sources (elements) arranged in a geometrical arrangement. The geometrical arrangement may be a sequence or a ring.

The geometrical arrangements of the UV and VIS/NIR light sources may be symmetrical about the spectrometer. The plurality of UV light sources (elements) can be arranged on opposite sides of the spectrometer. The plurality of VIS/NIR light sources (elements) can be arranged on opposite sides of the spectrometer. The UV light sources (elements) and the VIS/NIR light sources (elements) can be combined into a plurality of arrays, with one array on either side of the spectrometer.

The UV wavelengths may include wavelengths between 360 and 405 nm.

The VIS/NIR wavelengths may include wavelengths between 450 and 900 nm. The VIS/NIR wavelengths may include broadband wavelengths, i.e., including a continuous spectrum of wavelengths.

The light source may include a plurality of (linear) polarizers oriented in mutually the same direction.

The apparatus housing may further include an attachment ("cup") to accommodate the plant product, optionally wherein the cup includes a non-linear circumference (i.e., a plurality of folds). The cup may block the spectrometer from background light.

The cup may include an internal plant product holder for holding the plant product at a selected distance from spectrometer, optionally wherein the internal plant product holder includes two or more fins.

The apparatus may include a transmitter for transmitting the spectra and/or the calculated value via a wired or wireless data communications interface, e.g., via USB, Wi-Fi, Bluetooth and/or near-field communication (NFC).

The present invention further provides an attachment for accommodating at least a portion of a plant product to detect one or more properties of the plant product, the apparatus including:
a first portion configured to fasten to a spectrometer system; and
a second portion, connected to the first portion, configured to accommodate the portion of the plant product, wherein the second portion has concertina walls providing a flexible cross-section.

The present invention also provides a method for detecting one or more properties of a plant product, the method including:
(manually) fastening a first portion of an attachment for accommodating at least a portion of the plant product to a spectrometer system;
accommodating the portion of the plant product in a second portion of the attachment, and
transmitting a portion of light the plant product to the spectrometer system.

BRIEF DESCRIPTION OF THE DRAWINGS

Some embodiments of the present invention are hereinafter described, by way of example only, with reference to the accompanying drawings, in which.

DETAILED DESCRIPTION

Overview

Figure 1:
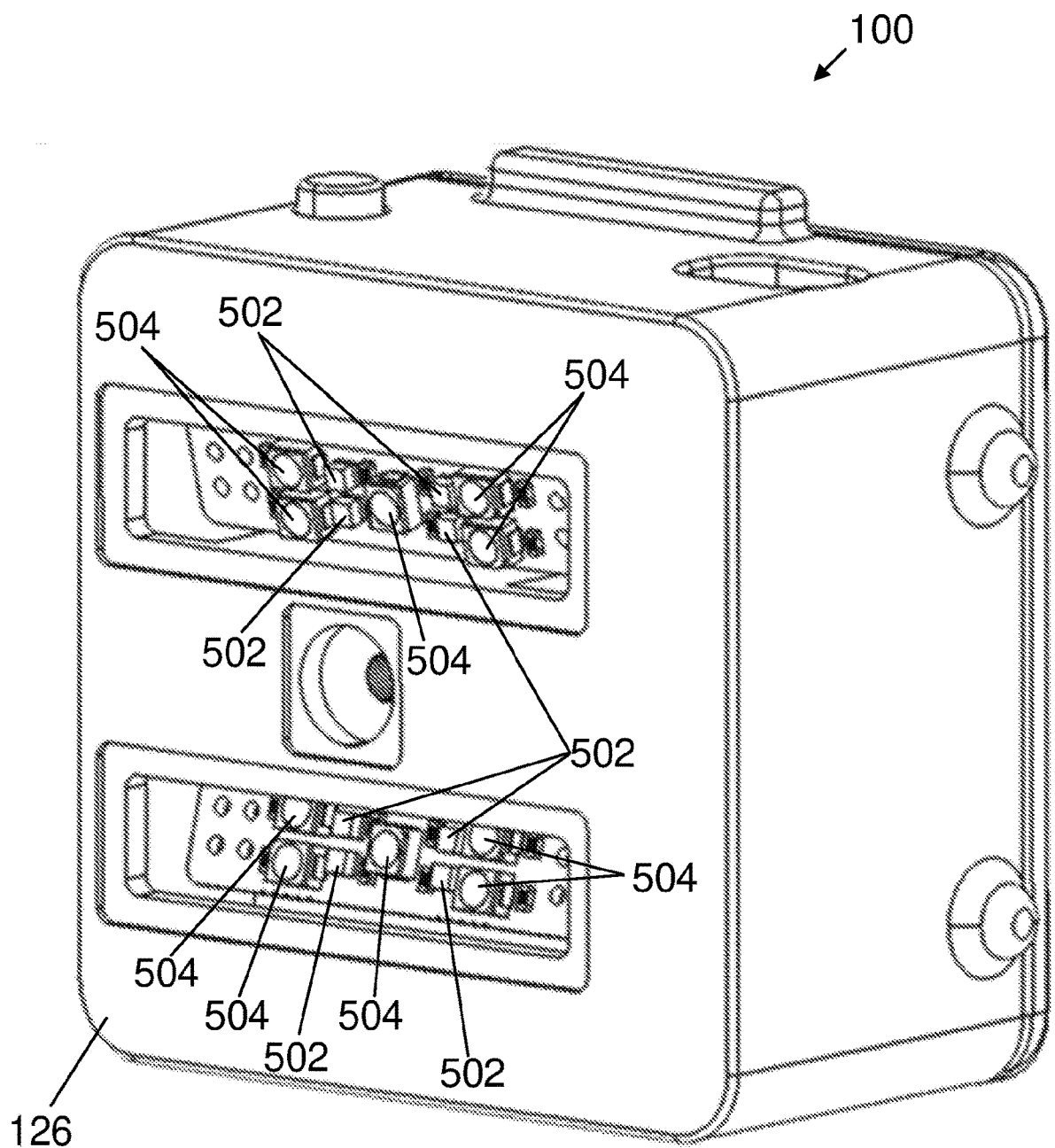
FIG. 1 is a perspective drawing of an embodiment of an apparatus.

Described herein is an apparatus 100 (which may be referred to as a "detecting apparatus") and a method 200 for detecting at least one property of a plant product 108, the at least one property including fluorescence and/or reflection of the plant product 108. In this context, the term "plant product" refers to any natural product of flora, and can include a fruit/vegetable, a fruit, a vegetable, a leaf, a stem, a root and/or a flower.

When polarized light interacts with a surface of the plant product 108, two processes may occur, corresponding to the wavelengths of the incident light: 1) fluorescence when the light has UV wavelengths, and 2) scattering/reflection when the light has UV and/or VIS/NIR wavelengths. The fluorescence process includes the absorption of a UV photon by outer shell electrons in molecules or compounds of the surface and subsequent relaxation giving rise to secondary photon emission at a longer wavelength (typically in the VIS/NIR region). The secondary emission is uncorrelated with the absorption: the fluorescence process is a random process and produces unpolarized light. The scattering/reflection causes specular reflection and diffuse reflection. Specular reflection of incident light maintains the polarization of the incident light. Diffuse reflection of the incident light contributes to de-polarization of the incident light due to the random angular distribution of the reflecting surfaces. By illuminating the surface with polarized incident light, light emitted from the surface that is caused by fluorescence and diffuse reflection (largely unpolarized) can be distinguished from light caused by specular reflection from the surface (polarized), as well as the polarized incident light itself.

The VIS/NIR region of the electromagnetic (EM) spectrum includes wavelengths in the visible and NIR regions of the EM spectrum. This may include wavelengths in a range, for example, of 380 nm to 2500 nm. Reference herein to "VIS/NIR wavelengths" includes one or more wavelengths in this range.

In performing the method 200, the apparatus 100 measures (thus generates) both fluorescence and diffuse reflection spectra of a region 106 of the plant product 108. The fluorescence and diffuse reflection spectra of the region 106 may be measured sequentially, e.g., measurement of the fluorescence spectrum is followed by measurement of the diffuse reflection spectrum (also referred to as the "reflection spectrum"), or vice versa. The fluorescence and reflection spectra may also be measured simultaneously, i.e., at the same time, so that the fluorescence and reflection of the region 106 can be determined rapidly without moving the plant product 108 relative to the apparatus 100. This region 106 is referred to as an "illuminated region" because it is illuminated by source light 104 from a light source 102. This region 106 is also referred to as a "target area", "target region", "test region", "measured region" or "emission region" because the source light 104 causes emission by the region 106 due to both the fluorescence and the diffuse reflection ("emission" in this context includes depolarizing reflection by the region, i.e., diffuse multiple reflection (scattering) by molecules of the plant product 108), and this emission creates emitted light 116 that is measured (i.e., "tested") by a spectrometer 118 (i.e., the emitted light 116 is caused by the source light 104 being directed onto the region 106). The fluorescence and/or the reflection of the region 106 may be the pigment fluorescence and/or natural reflection of the region 106 of the plant product 108.

Figure 3:
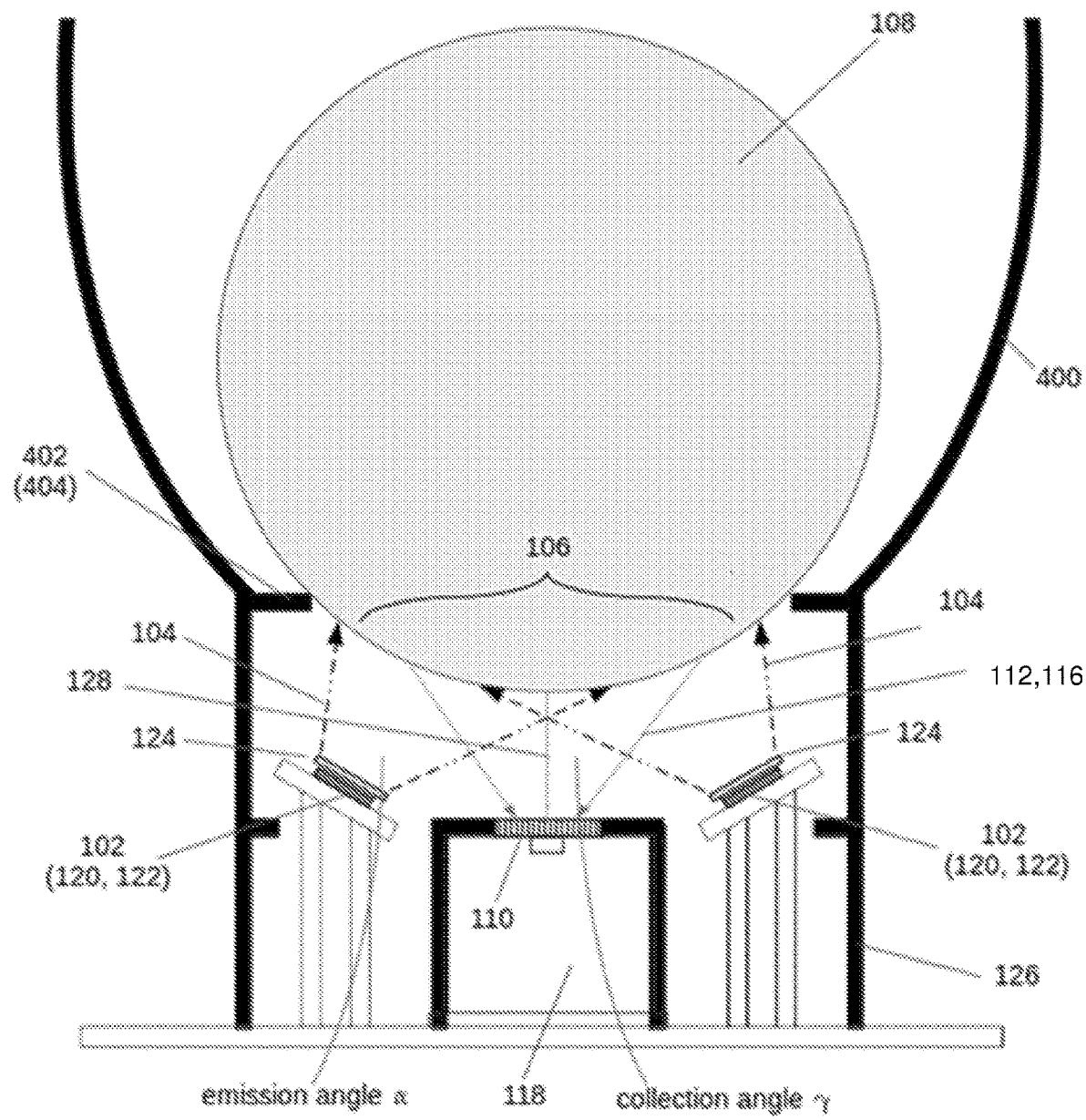
FIG. 3 is a schematic diagram of a geometry of the apparatus and a plant product.

As shown in FIG. 3, the apparatus 100 may include:
a. a light source 102 for directing the source light 104 including UV light at UV wavelengths and polarized VIS/NIR light at VIS/NIR wavelengths onto the region 106 of the plant product 108;
b. a spectrometer polarizer 110 arranged for blocking the polarized VIS/NIR light of the source light 104 and polarized specular reflection 112 from the region 106, and for transmitting a portion of emitted light 116 caused by fluorescence and/or diffuse reflection from the region 106 of the plant product 108; and
c. a VIS/NIR spectrometer 118 for receiving the transmitted portion.

Figure 2:
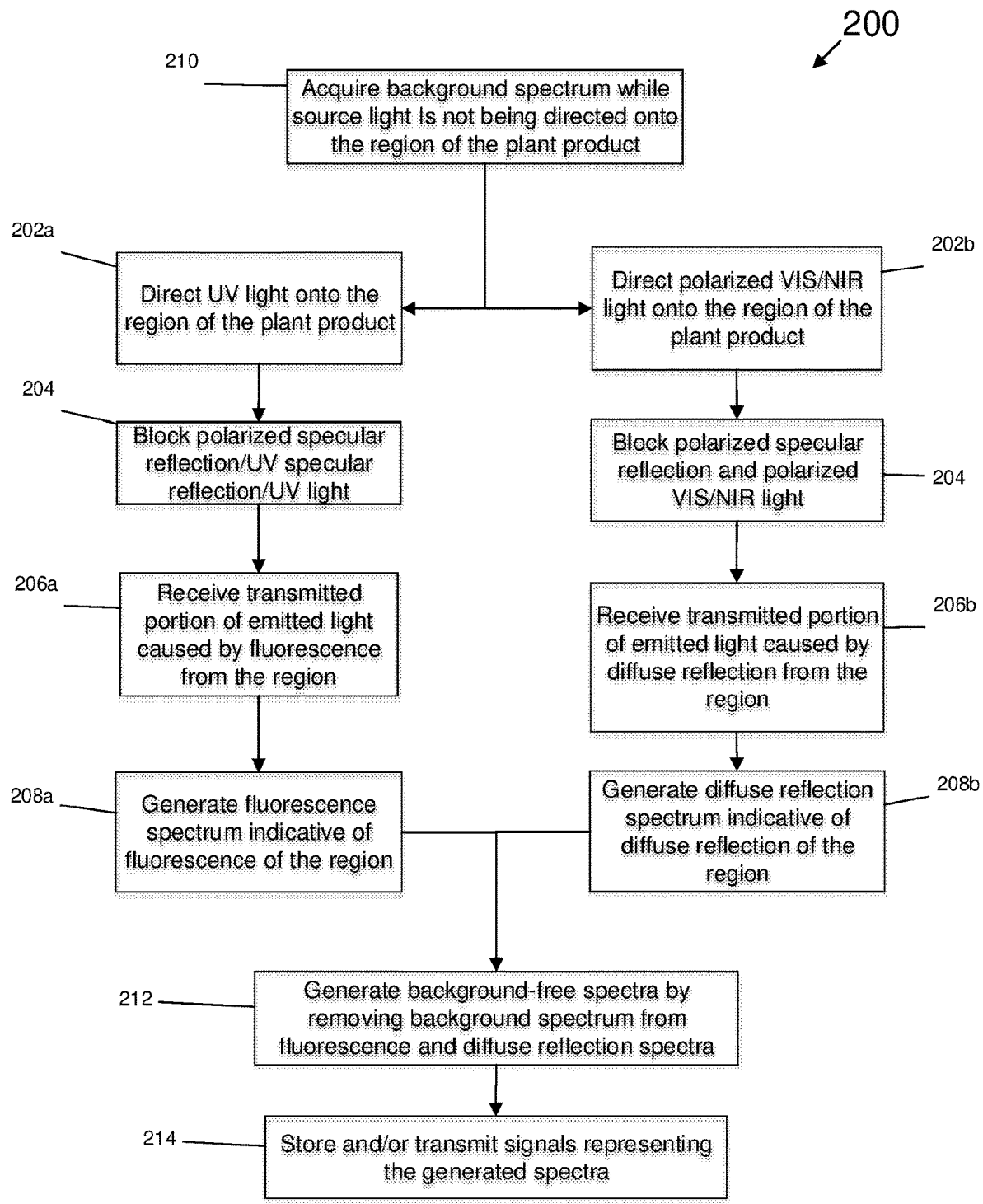
FIG. 2 is a flowchart of a method performed by the apparatus.

As shown in FIG. 2, the method 200 may include:
a. directing the source light 104 including the UV light at UV wavelengths and the VIS/NIR light at VIS/NIR wavelengths onto the region 106 of the plant product 108 (steps 202a, 202b);
b. blocking the polarized VIS/NIR light of the source light and polarized specular reflection 112 from the region 106 (step 204); and
c. transmitting the portion of the emitted light 116 caused by the fluorescence and/or the diffuse reflection from the region 106 of the plant product 108 to the spectrometer 118 (steps 206a, 206b).

In some embodiments, the UV light is polarized UV light. The polarized UV light has the same polarization (i.e., polarization orientation or direction) as the polarized VIS/NIR light. In these embodiments the source light 104 can be referred to as "polarized source light". The blocking can further include blocking the polarized UV light.

In some embodiments a UV filter blocks the UV light of the source light 104 and the scattered/reflected UV light. The UV filter transmits a portion of the emitted light 116 at VIS/IR wavelengths.

The polarized specular reflection 112 includes light caused by the polarized VIS/NIR light being specularly reflected from the region 106. Where the UV light is polarized UV light, the polarized specular reflection 112 also includes light caused by the polarized UV light being specularly reflected from the region 106. The polarized specular reflection 112 has the same polarization as the polarized VIS/NIR light because the process of specular reflection preserves polarization.

The emitted light 116 is substantially unpolarized because the mechanisms of fluorescence and diffuse reflection in the region 106 do not preserve polarization; thus the emitted light 116 includes a plurality of random polarizations, which can be decomposed into a polarization parallel to the polarization of the source light 104 and a polarization perpendicular to the polarization of the source light 104 in equal amounts. The transmitted portion of the emitted light 116 has an opposite polarization from the polarized VIS/NIR light of the source light 104. The polarized VIS/NIR light and the polarized specular reflection 112 are blocked by the spectrometer polarizer 110: accordingly, the spectrometer polarizer 110 can be referred to as a "polarizing filter". Where the UV light is polarized UV light the spectrometer polarizer 110 blocks the polarized UV light. The transmitted portion (amounting to about a half of the emitted light 116) is transmitted by the spectrometer polarizer 110. The spectrometer polarizer 110 is a crossed polarizer to the polarization of the VIS/NIR light of the source light 104. Use of a crossed polarizer may ensure that most source light 104 that is polarized (e.g., the polarized VIS/NIR light, or in some embodiments the polarized VIS/NIR light and the polarized UV light), i.e., polarized source light that has not interacted with the region 106 at all (referred to as "stray light"), is not transmitted to the spectrometer 118, as well as much of the polarized specular reflection 112 that has only interacted with the skin of the plant product 108 (which largely maintains the polarization of the polarized source light). Conversely, the transmitted portion is a fraction of the emitted light 116 that is caused by fluorescence and diffuse reflection from the region 106, which is depolarized (the fraction is approximately 50% of the emitted light 116 if the emitted light 116 is completely unpolarized). The depolarized emitted light 116 has undergone random reflection processes in the skin or outer flesh layers of the plant product 108.

The arrangement of the spectrometer polarizer 110 reduces light being received by the spectrometer 118 that has not been affected by the fluorescence or diffuse reflection of the region 106 (e.g., the polarized VIS/NIR light of the source light 104 and the polarized specular reflection 112): such light is undesirable because it is not indicative of the properties of the plant product 108, and because it can obscure the emitted light 116 (e.g., by saturating sensor elements in the spectrometer polarizer 110) which is indicative of the properties of the plant product 108. The wavelengths of the source light 104 and the wavelengths of the emitted light 116 caused by the fluorescence and/or the reflection can substantially overlap, e.g., they can both include wavelengths in the visible range, but the crossed-polarizer arrangement of the spectrometer polarizer 110 can still block the undesirable light.

As shown in FIG. 2, the method 200 can include: (a) first, illuminating the region 106 with the UV light at step 202a, receiving fluorescence emission at the spectrometer 118 at step 206a, and generating by the spectrometer 118 a fluorescence spectrum indicative of fluorescence of the region 106 at step 208a; and (b) second, illuminating the region with polarized VIS/NIR light at step 202b, receiving diffuse reflection emission at the spectrometer 118 at step 206b, and generating by the spectrometer 118 a diffuse reflection spectrum indicative of diffuse reflection of the region at step 208b. In these embodiments, the VIS/NIR light is not emitted from the light source 102 during steps 202a, 206a and 208a, and conversely, the UV light is not emitted from the light source 102 during steps 202b, 206b and 208b. Alternatively, in performing the method 200, the apparatus 100 may measure both fluorescence and diffuse reflection spectra of the region 106 simultaneously, i.e., at the same time, which can be faster than taking spectra at different times: i.e., the fluorescence and diffuse reflection do not need to (or cannot) be measured at different times.

Light Source

The light source 102 may include a plurality of sources including: a UV source 120 for generating the UV light, and a VIS/NIR source 122 for generating the VIS/NIR light.

The generated UV light may be in a UV wavelength range from 360 to 405 nanometers (nm). The generated VIS/NIR light may be in a VIS/NIR wavelength range from 450 to 1100 nm.

UV light generated by the UV source 120 may be in a UV power range from 10 to 350 milliwatts (mW). VIS/NIR light generated by the VIS/NIR source 122 may be in a VIS/NIR power range from 100 to 500 mW.

As shown in FIG. 1, the UV source 120 can include a plurality of UV sources (these may be referred to as "UV elements 502" of the UV source 120), and the VIS/NIR source 122 can include a plurality of VIS/NIR sources (these may be referred to as "VIS/NIR elements 504" of the VIS/NIR source 122). The UV elements 502 each generate light in the UV wavelength range. The VIS/NIR elements 504 each generate light in the VIS/NIR wavelength range. Each UV element 502 may generate UV light in a power range from 10 to 350 mW. Each VIS/NIR element 504 may generate VIS/NIR light in a power range from 100 to 500 mW. The pluralities of the UV and VIS/NIR sources can provide more illumination of the region than single UV and VIS/NIR sources at the same individual output power, and the total illumination power can be varied over a greater power range by turning individual elements off and on.

Each UV element 502 may be a surface mount device which enables efficient heat dissipation. Each UV element 502 may be substantially 1 mm in diameter. Each UV element 502 may be a commercially available UV LED light, e.g., a Nichia NCSU275T-U405 UV LED 2-Pin Surface Mount package, which provides a peak wavelength of 405 nm and a radiant flux of 370 mW for 500 mA current.

Each VIS/NIR element 504 may be a surface mount device which enables efficient heat dissipation. Each VIS/NIR element 504 may be substantially 5 mm in size or diameter. Each VIS/NIR element 504 may be a commercially available white LED or broadband NIR light source, for instance a Cree® PLCC4 SMD LEDCLA1B-WKW/MKW (white) or an OSRAM SYNIOS® P2720, SFH 4776 broadband emitter.

In some embodiments, each UV element 502 and each VIS/NIR element 504 may be a semiconductor laser. In other embodiments, each UV element 502 and each VIS/NIR element 504 may be an incandescence lamp.

The pluralities of UV and VIS/NIR sources 502,504 may be arranged in a geometrical arrangement about the spectrometer 118. Preferably the geometric arrangement is symmetrical about an axis of the spectrometer 118 such that the pluralities of UV and VIS/NIR sources 502,504 uniformly illuminate the region 106 of the plant product 108. The geometrical arrangement may be chosen to optimise space on a printed circuit board (PCB) of the apparatus 100, e.g., based on the size of the UV sources 502 and the VIS/NIR sources 504. For example, the sources 520, 504 may be arranged adjacently to each other, including as close as possible while remaining on the same PCB and not obscuring each other's emissions.

As shown in FIG. 1, in some embodiments, the plurality of UV elements 502 and the plurality of VIS/NIR elements 504 can be arranged on opposite sides of the spectrometer 118. In certain embodiments there may be a combination of UV elements 502 and VIS/NIR elements 504 on either side of the spectrometer 118. The elements 502,504 can be arranged in one or more arrays. For example, on each side of the spectrometer 118, there may be five VIS/NIR elements 504 and four UV elements 502. The VIS/NIR elements 504 can be arranged in a quincunx (i.e., in a cross arrangement with four elements 504 at the corners of a square or rectangle and the fifth at its centre), and the UV elements 502 may be arranged in a square or rectangle that is centred on the central VIS/NIR element, e.g., such that the UV elements are inside a square or rectangle formed by the four outer VIS/NIR elements. An arrangement of elements 502,504 on either side of the spectrometer 118 may be more efficient for blocking undesirable light by the spectrometer polarizer 110 (e.g., the polarized VIS/NIR light of the source light 104, the polarized specular reflection 112).

The elements may be symmetrically (by reflection symmetry) arranged on either side of the spectrometer 118. This may improve the blocking of the undesirable light by the spectrometer polarizer 110. There may be at least one element on each side of the spectrometer 118. The at least one element on each side of the spectrometer 118 can be arranged in a plane that is parallel to a direction defined by the polarization of the spectrometer polarizer 110, i.e., the elements can be arranged in a plane with a normal vector that is perpendicular to the polarization of the spectrometer polarizer 110. For example, the elements can be arranged along a line that is defined by the polarization direction of the spectrometer polarizer 110 and intersects the centre of the spectrometer 118.

Figure 6:
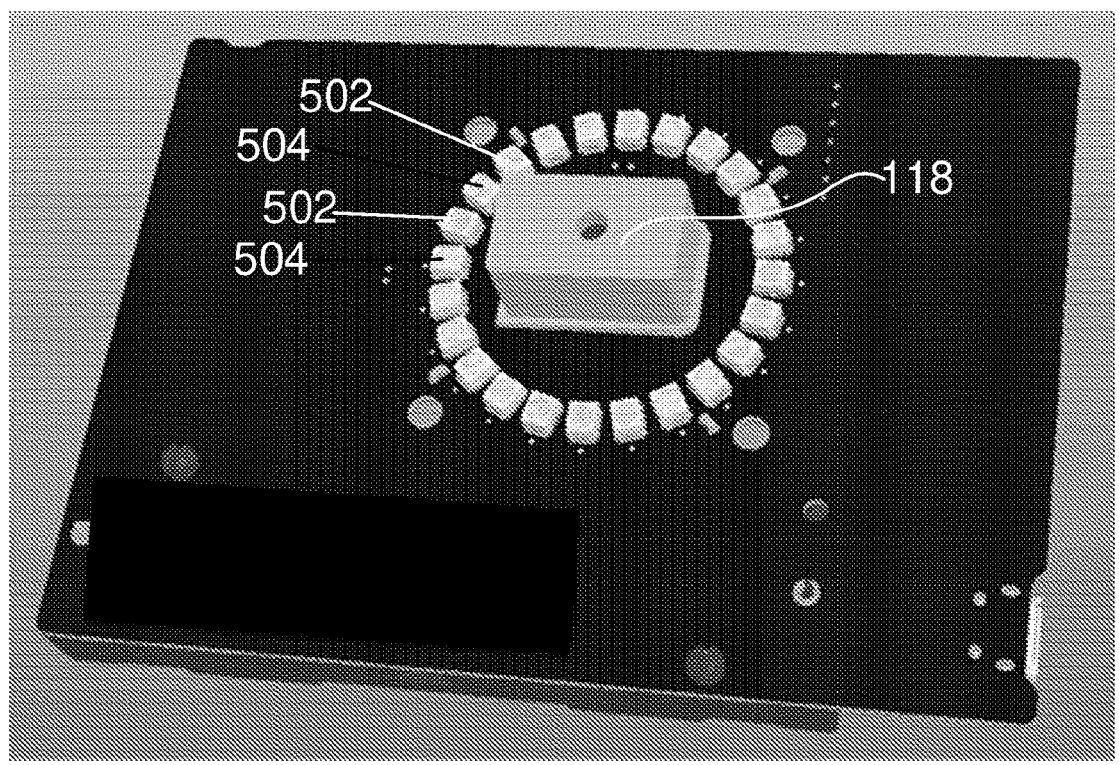
FIGS. 6 and 7 respectively show a perspective drawing and a plan diagram of a second side of a PCB in an alternative embodiment of the apparatus.
Figure 7:
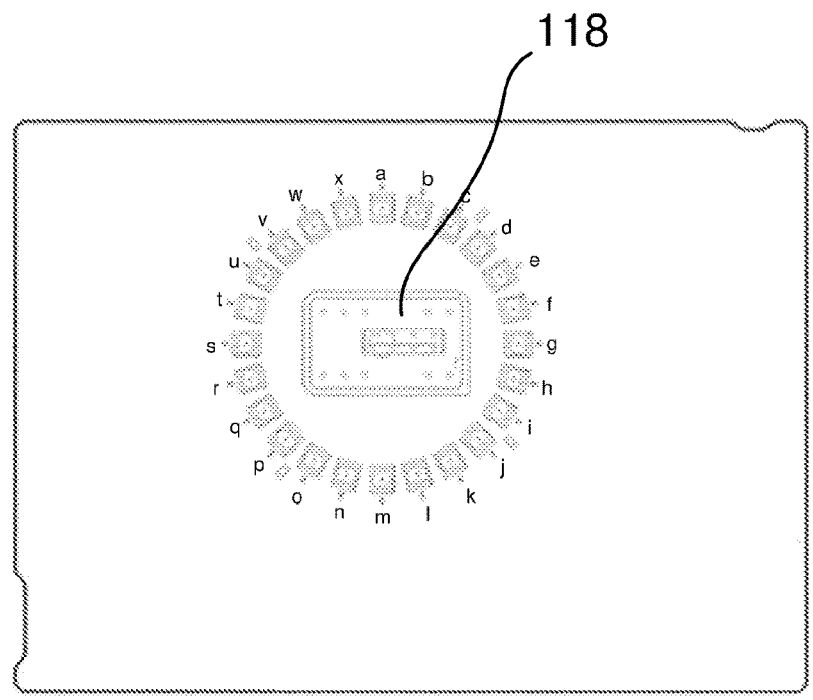

As shown in FIGS. 6 and 7, in some embodiments, the plurality of UV elements 502 can be arranged in a ring around the spectrometer 118; similarly, the plurality of VIS/NIR elements 504 can be arranged in a ring around the spectrometer 118. The apparatus 100 can thus include the plurality of UV elements 502 and the plurality of VIS/NIR elements 504, and both rings can be next to or around the spectrometer 118 and can be centred on the spectrometer 118. The UV elements 502 can be interleaved with the VIS/NIR elements 504 so that the UV ring and the VIS/NIR ring overlap spatially, and so that the rings are substantially equal in diameter. For example, in FIG. 7, the plurality of UV elements 502 may be those labelled {a, c, e, g, i, k, m, o, q, s, u, w} and the plurality of IR/VIS elements 504 may be those labelled {b, d, f, h, j, l, n, p, r, t, v, x}.

The plurality of VIS/NIR elements 504 can include at least one white light element and/or at least one broadband NIR light element. For example, the white light LEDs can be and "cold white" or "warm white" (which both emit light at visible wavelengths, e.g., from 400 to 750 nm). The cold white light LEDs may have a higher colour temperature than the warm white light LEDs. Each white light LED may be a commercially available LED light, e.g., a Cree® CLA1B-WKW/MKW PLCC4 SMD LED.

The light source 102 may include a source polarizer 124 to polarize the polarized VIS/NIR light of the source light 104. The source polarizer 124 and the spectrometer polarizer 110 are oriented to have perpendicular polarizations, and so can be referred to as "crossed polarizers". The source polarizer 124 can be referred to as a "polarizing filter".

In some embodiments, the source polarizer 124 also polarizes the polarized UV light of the source light 104.

The source polarizer 124 can be a linear polarizer (thus the spectrometer polarizer 110 is correspondingly a linear polarizer). The source polarizer 124 can also be a circular polarizer (thus the spectrometer polarizer 110 is correspondingly a circular polarizer with an opposite direction).

The source polarizer 124 can include a plurality of polarizer elements corresponding to one or more of the plurality of VIS/NIR elements 504. If the source polarizer 124 also polarizes the UV light of the source light 104, then the plurality of polarizer elements may also include polarizer elements that correspond to the plurality of UV elements 502. The polarizer elements may be mutually oriented in the same direction: each polarizer element may be arranged in a first orientation on its corresponding element 502,504 so that the light illuminating the region 106 is polarized in a first direction perpendicular to the polarization direction transmitted by the spectrometer polarizer 110.

In some embodiments, the polarizer elements may be commercially available polarizing filters, e.g., Thorlabs LPVISE2×2—2"×2" Dichroic Film Polarizer Sheet or polarizers used for photography (such as non-optical grade polarizing films and sheets).

In some embodiments, the source polarizer 124 may include a single polarizer element with a shape corresponding to the geometric arrangement of the light source 102. This may be a single polarizer sheet or film cut to a size and shape corresponding to the geometric arrangement of the light source 102, e.g., appropriate to polarize the pluralities of UV elements 502 and VIS/NIR elements 504 in the geometric arrangement(s).

The source polarizer 124 may be aligned with the spectrometer polarizer 110 by arranging them such that the amount of light transmitted by the spectrometer polarizer 110 is minimised.

UV Filter

In some embodiments the apparatus 100 may include a UV filter for blocking the UV light of the source light 104 and UV specular reflection from the region 106, to prevent this light from being transmitted and received by the spectrometer 118. The UV filter transmits light with VIS/IR wavelengths to the spectrometer 118. The UV filter may be a long-pass filter that transmits light at wavelengths longer than the wavelengths of the UV light of the source light 104. The range of VIS/IR wavelengths transmitted by the UV filter may be different to the range of VIS/NIR wavelengths in the VIS/NIR light of the source light 104.

Housing and Cup

The method 200 may include protecting and holding the spectrometer 118 in a protective housing 126.

As shown in FIG. 1, the apparatus 100 may include the housing 126 for protecting the spectrometer during use. The housing 126 houses and mounts the spectrometer 118, the light source 102, the polarizers 110, 124 and electronics of the apparatus 100. The housing 126 can include a baffle to shield the spectrometer 118 from the source light 104.

The apparatus 100 may be a portable, hand-held device for use in a field or orchard. In the portable device, the housing can include or form a handle or grip to be held by a person's hand.

Also described herein is an attachment for accommodating at least a portion of a plant product to detect one or more properties of the plant product. The attachment can include:

a first portion configured to fasten to a spectrometer system (e.g., including the VIS/NIR spectrometer 118), e.g., to a nozzle of spectrometer system; and a second portion, connected to the first portion, configured to accommodate the portion of the plant product. As further described hereinafter, the second portion can have concertina walls providing a flexible cross-section. The attachment may be referred to as an "attachment" because it attaches to the spectrometer system, and/or as a "cup" because it cups the plant product, and/or as a "shroud" because it covers or envelops the relevant portion of the plant product so as to conceal from external background light (thus concealing it from view).

The apparatus 100 may further include the cup ("fruit cup") for accommodating the portion of the plant product 108 (i.e., such that the cup is integral with the housing 126).

Figure 4:
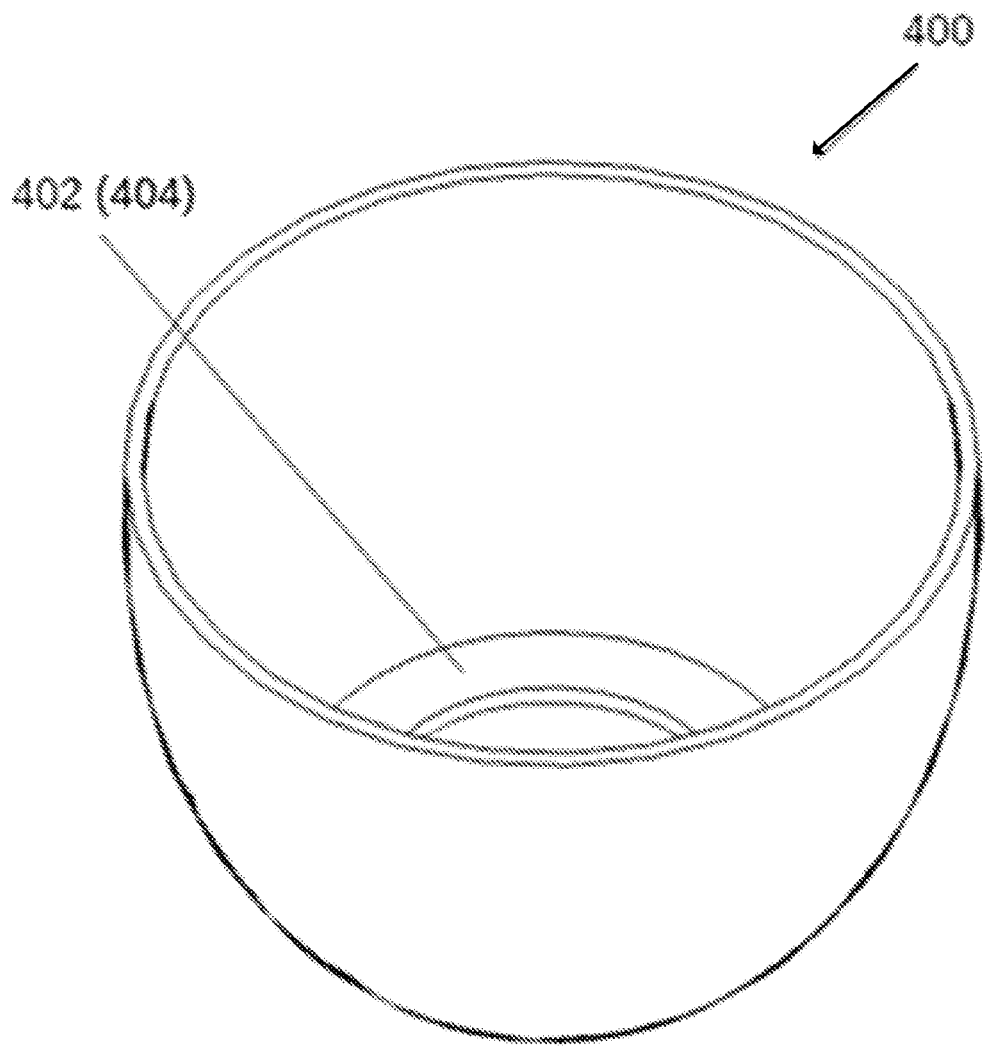
FIG. 4 is a perspective drawing of a first embodiment of an attachment ("cup") of the apparatus to hold the plant product during performance of the method.

As shown in FIGS. 3 and 4, an embodiment of the cup 400 may be formed as a concavity in the housing.

The cup may be designed for a particular type or variety of the plant product 108, so there may be different cups of different sizes and shapes for different types/varieties of plant products (accordingly, the apparatus 100 can be used for different crops without changing the optical arrangement). The cup may be larger than the plant product 108 so that the plant product 108 may be enclosed inside the cup to substantially block background light (such as sunlight or other environmental light) from entering the spectrometer 118, i.e., the cup blocks the spectrometer from background light. The cup includes visible/infrared light-blocking material and light-absorbing material, e.g., a naturally black material, e.g., a polymer, and/or a black paint or layer applied to the inside and/or outside surfaces of the cup.

Figure 8:
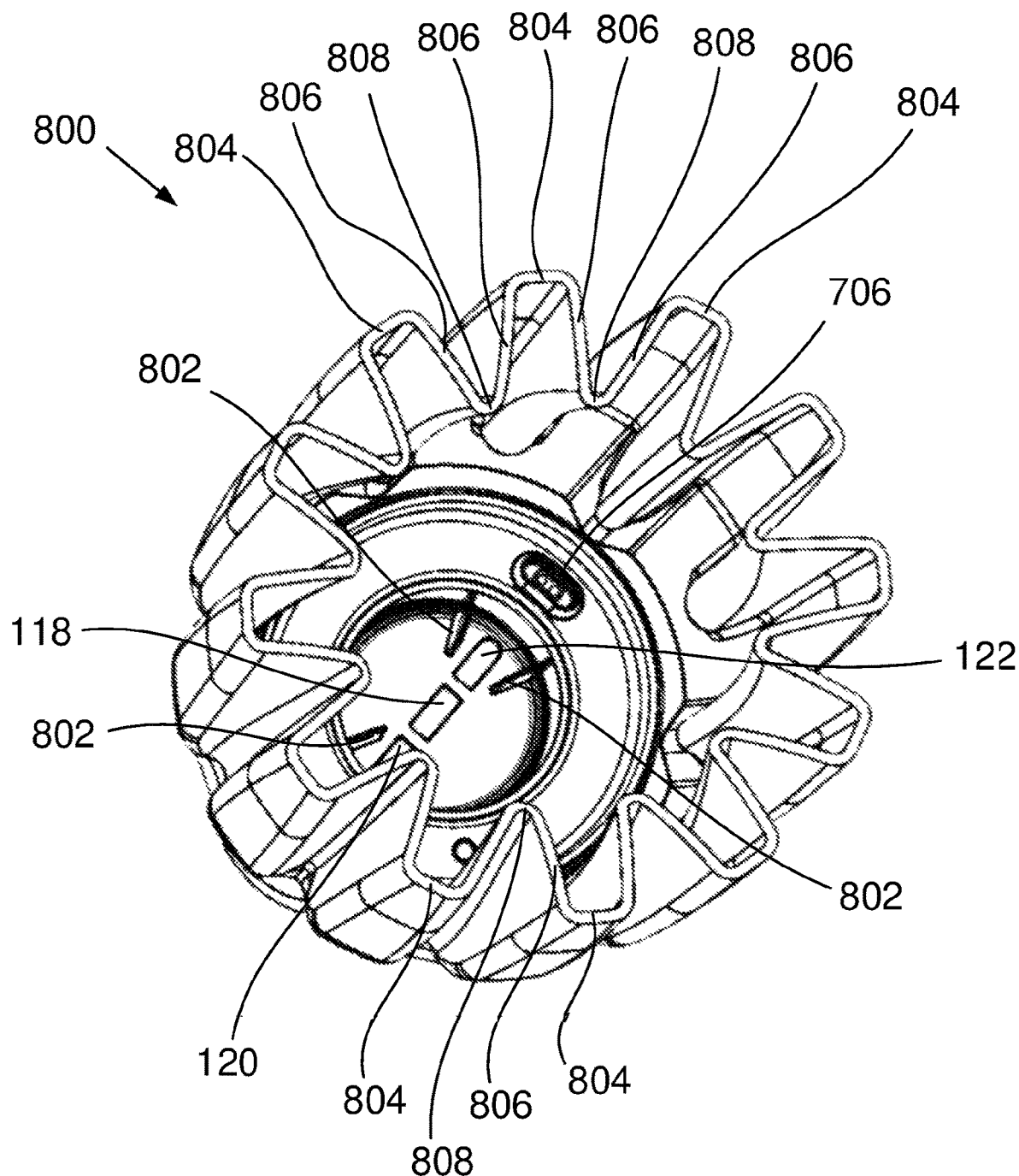
FIG. 8 is a perspective drawing of a second embodiment of the cup.

Alternatively or additionally, as shown in FIG. 4, an embodiment of the cup 400 may include a flexible seal 402 that contacts the plant product 108 around the region 106 and that substantially blocks background light from reaching the region 106. The flexible seal 402 may form a polymer aperture inside the cup 400. The housing 126 or the cup may include an internal plant product holder (in the form of spacer) 404 for holding the plant product 108 such that the region 106 is at a selected distance (or "set distance") from, and/or at a selected location relative to, the spectrometer 118. The selected distance may be approximately 10 mm. This means that each time a new plant product 108 (of the same type or variety) is used with the apparatus 100, the region 106 is substantially the same for exemplary plant products of substantially consistent shape and size. Thus the region 106 is effectively selected by holding the plant product 108 in the internal plant product holder 404. The flexible seal 402 may form the internal plant holder 404 if the seal is firm enough to hold the plant product 108 with the region 106 at the selected distance. As shown in FIG. 8, the internal plant product holder 404 may include a plurality of fins 802. Each fin 802 is a flattened projection extending in a radial direction towards a centroid or centre point aligned with a central axis 128 defined by the centre of a spectrometer slit of the spectrometer 118. Each fin 802 has a first end that is attached to the housing 126 or the cup, and a second end closer to the centroid or centre point. Each fin 802 can have a length of approximately 10 mm (i.e., extending in the radial direction). Each fin 802 can have a height of approximately 18 mm (i.e., extending in a direction substantially parallel to the central axis 128). Each fin 802 can have a thickness of approximately 2 mm (perpendicular to its length and height). At least a portion of the fins 802 are co-planar. For example, for each of the portion of co-planar fins 802, an outer edge of each fin 802 that is furthest from the spectrometer 118 can lie in a single plane. Example dimensions for the fruit cup are: lower diameter, 40 mm; upper diameter, 85 mm; height, 90 mm; set distance, 10 mm; inner diameter of the flexible seal, 50 mm.

The cup 400 may be integral with the housing 126; alternatively, the cup 400 may be separably attached to the housing 126. The cup can be detachable from the housing 126, e.g., so that the cup can be replaced in the event it is damaged, e.g., including a screw or clip on the housing 126 or the cup, e.g., to fasten the cup onto a rim of the housing 126.

As mentioned above, the second portion of the cup can have concertina walls providing a flexible cross-section. In such embodiments, the cup may be described as a flexible cup 800. The first portion and/or the second portion can include a naturally flexible/resilient/elastic material. The concertina walls of the second portion can have a non-linear circumference, i.e., a plurality of folds, i.e., a plurality of changes in direction of the circumferential wall such that the radius changes substantially as the angle around the central axis changes. The concertina walls can extend axially, i.e., along the central axis of the cup 800, such that the concertina walls are substantially parallel to the central axis in the second portion, and narrowing to the spectrometer system in the first potion, thus forming a tapered or tulip profile when held vertically (with the central axis vertical). The second portion may be referred to as a "concertina cylinder". The non-linear circumference and naturally flexible/resilient/elastic material provide the flexible cross-section (or naturally variable cross-section) for the cup 800. Having the flexible cross-section means the cross-section of the cup 800 naturally adapts, i.e., increases in average diameter, due to outward pressure/forces applied by the plant product (when the plant product is inside the cup 800) to a radially inner circumference of the cup 800, thus "cupping" or holding plant products of mutually different sizes. The flexibility of the flexible cross-section is sufficient so that the fruit can apply the outward pressure/forces without substantially damaging or affecting the fruit, e.g., its skin. In other words, having the flexible cross-section may allow the cup 800 to reduce an amount of force applied to the plant product by the cup 800 (in response to the outward pressure/forces applied by the fruit), and thereby reduce the risk of the plant product being bruised or otherwise damaged when being scanned using the apparatus 100—compared with the use of a cup made of a hard/inflexible material (e.g., hard plastic) and/or having an inflexible cross-section i.e., a cross-section without natural variability.

The naturally flexible/resilient/elastic material of the cup 800 may include a food-grade flexible/resilient/elastic material, e.g., a thermoplastic elastomer.

Figure 9B:
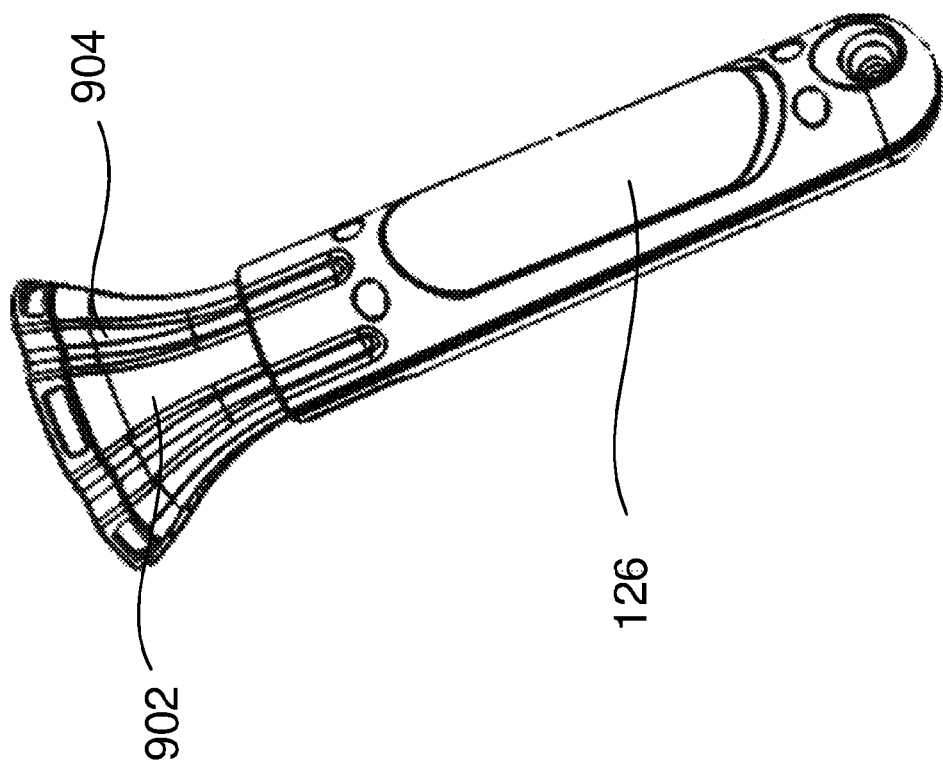
FIG. 9B is a perspective drawing of the apparatus without the cup.
Figure 9A:
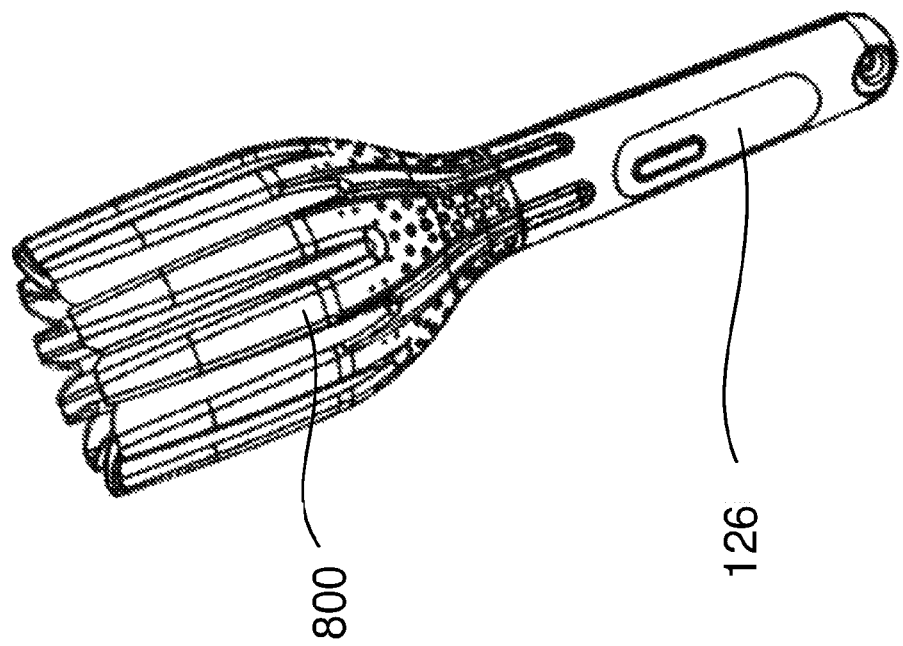
FIG. 9A is a perspective drawing of the apparatus including the cup in place; and i.

The first portion of the cup is configured to fasten to the spectrometer system. The spectrometer system may include at least the VIS/NIR spectrometer 118 as described herein. As shown in FIGS. 9A and 9B, in some embodiments, the first portion of the cup 800 is configured to removably attach or fasten to a nozzle of the housing 126, e.g., in the form of a flange 902. FIG. 9A shows the cup 800 fastened to the flange 902, while FIG. 9B shows the flange 902 without the cup 800 fastened or attached (i.e., the cup 800 is removed). The flange 902 is a substantially non-malleable and may be made of hard plastic. In the embodiment shown, the flange 902 is part of the housing 126. The first portion can be flexible so that a user can fasten the first portion to the spectrometer system by manually adapting (e.g., stretching) it onto the flange 902. Once the user has adapted the first portion onto the flange 902, the first portion securely grips the flange 902 such that the cup 800 is unlikely to be removed from the flange 902 without a user manually adapting (pulling) the first portion in order to remove the cup 800. The secure grip of the first portion on the flange 902 may be at least in part due to the resilient material of the first portion and/or a material of the flange. The flange 902 may include one or more grip portions 904 to improve the grip of the first portion on the flange 902. The grip portions 904 can include one or more depressions and/or notches.

As shown in FIG. 8, the concertina/bellow shape/profile of the cup 800 includes a plurality of outer circumferential portions 804 along a radially outer circumference centred on the central axis 128, wherein adjacent ones of the outer circumferential portions 804 are connected by an indent portion that includes two inwardly extending walls 806 joining at an inner circumferential portion 808 on the radially inner circumference centred on the central axis 128. The plurality of inner circumferential portions 808 form respective troughs. The outer circumferential portions 804 may be evenly spaced along the outer circumference, and the inner circumferential portions 808 may be evenly spaced along the inner circumference. A radius of the inner circumference is smaller than a radius of the outer circumference. The non-linear circumference is formed by the outer circumferential portions 804 connected to the inwardly extending walls 806 connected to the inner circumferential portions 808.

The bellow shape of the cup 800 allows the cup 800 to be used with fruits/vegetables of different sizes. For example, the cup 800 may be capable of use with fruits/vegetables of with a size anywhere between a plum and a pineapple, while still maintaining light-proof conditions required for an accurate measurement. As the cup 800 is flexible, the concertina/bellow shape/profile can be displaced by a plant product being accommodated within the cup 800.

The shape/profile of the cup 800 may make it easier for the user to reach and scan fruits/vegetables that are still growing on trees and which may be somewhat obstructed by branches or leaves. As the cup 800 is a flexible cup it can adapt to an irregular shape of the plant product. The flexibility of the cup 800 may reduce the risk of accidentally plucking the plant product from the tree because the amount of force applied to the plant product by the cup 800 is sufficiently small. Further, the cup 800 can adapt (e.g., fold, due to the flexible/naturally variable cross-section) when and where it comes into contact with a branch, while also maintaining light-proof conditions when the apparatus is used with a plant product attached close to the branch, i.e., preventing background light from reaching the region of the plant product and/or the spectrometer 118. Alternatively, the apparatus 100 can be a fixed device which can be used in fruit graders. In this embodiment, the housing 126 may be a light proof enclosure.

Example dimensions of the cup 800 include a wall thickness of 2 mm; a cup depth of 95 mm; the radius of the outer circumference of 90 mm; and the radius of the inner circumference of 60 mm. A distance between an adjacent outer circumferential portion 804 and inner circumferential portion 808 can be approximately 15 mm. As shown in FIG. 8, the plurality of folds may include U shaped folds (formed by the outer circumferential portions 804 and adjacent ones of the inwardly extending walls 806) and V shaped folds (formed by the inner circumferential portion 808 and adjacent ones of the inwardly extending walls 806), including a selected number of the U shaped folds around the outer circumference and the same number of the V shaped folds around the inner circumference, wherein the selected number may be approximately 12 or 12.

When the cup 800 is at rest, i.e., not accommodating a plant product, the radius of the outer circumference can be approximately 90 mm. When the cup 800 is used to accommodate a plant product therein, the diameter of the outer circumference may increase to approximately 140 mm as the bellow shape expands to accommodate the plant product. As the cup 800 is a flexible cup, the cup can deform when accommodating a plant product, e.g., to an elliptical shape with a maximum major axis of approximately 180 mm.

Spectrometer

The spectrometer 118 is configured to detect light intensity in the UV to NIR spectrum (e.g., 300-1000 nm).

The spectrometer 118 may generate one or more spectra that are indicative of the transmitted portion, e.g., the fluorescence spectrum and diffuse reflection spectrum.

The spectrometer 118 receives the transmitted light that has passed through the spectrometer polarizer 110. The spectrometer polarizer 110 is arranged to block the polarized specular reflection 112 by selecting the orientation of the spectrometer polarizer 110 to be perpendicular to the polarization of the source polarizer 124. Where the source polarizer 124 includes one or more linear polarizing filters arranged in a first orientation, the spectrometer polarizer 110 may be a linear polarizing filter arranged in a second orientation that is perpendicular to the first orientation.

In some embodiments, the spectrometer 118 may be a commercially available mini-spectrometer, e.g., a Hamamatsu C12880MA mini-spectrometer or a Nano-Lamda NSP32 nano-spectrometer module.

Geometry

As shown in FIG. 3, the apparatus 100 has a geometry such that the spectrometer 118 receives the emitted light 116 from the region 106. The light source 102 is mounted on the apparatus 100 such that the source light 104 can simultaneously illuminate the region 106.

The UV source 120 may be aligned for the UV light to be emitted at an angle substantially equal to 25 degrees to a normal direction, where the normal direction aligns with the central axis 128 defined by the centre of a spectrometer slit of the spectrometer 118, around which the light source 102 is arranged. The VIS/NIR source 122 may be aligned for the VIS/NIR light to be emitted at an angle substantially equal to 25 degrees to the normal direction.

As shown in FIG. 3, the light source 102 (including the UV and VIS/NIR sources 120,122) emits light with an emission angle $\alpha$. The emission angle $\alpha$ may be substantially similar in magnitude to a collection angle $\gamma$ of the spectrometer 118. This may allow the spectrometer 118 to receive a sufficient intensity of light without using a collection lens or other optical system. Variations to the opening angle $\alpha$ may be determined depending on the plant product 108 and region 106 thereof being illuminated (and the cup 400 may be similarly configured to appropriately expose the position of the region 106). In some embodiments, the emission angle $\alpha$ can be substantially equal to 25 degrees.

As shown in FIG. 3, the spectrometer 118 may be substantially in (or at least overlapping with) the same plane as the light source 102.

Electronics and Signal Processing

Figure 5:
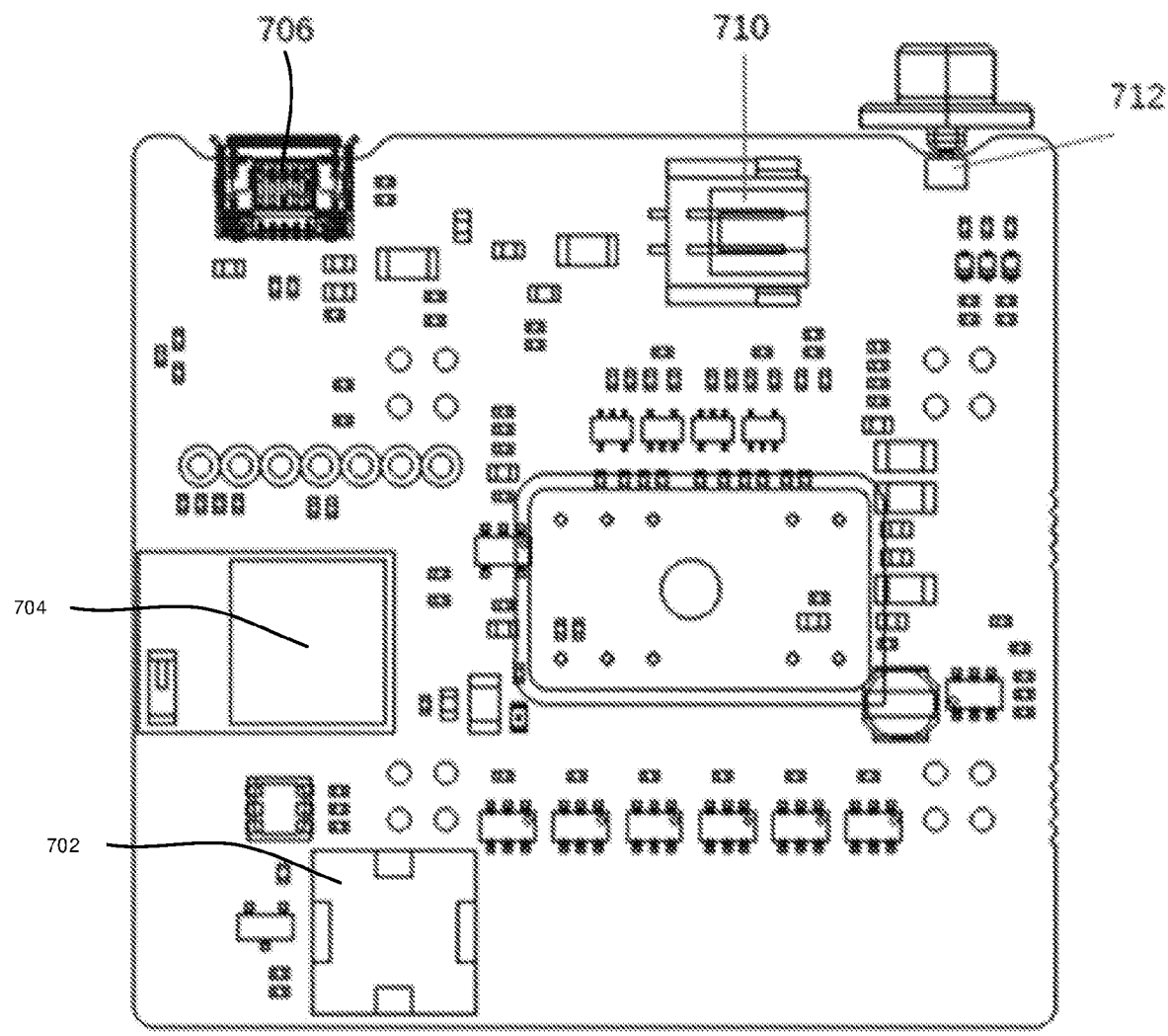
FIG. 5 is a plan diagram of a first side of a printed circuit board (PCB) of the apparatus.

The apparatus 100 may include electronics (i.e., electronic components). As shown in FIG. 5, the electronics may include a microprocessor 702 (with an integral memory) and a transmitter 704 for reading out, processing, storing and transmitting the generated spectra. The microprocessor 702 and transmitter 704 may include data communication interfaces. The transmitter 704 can transmit the signals to a local terminal computing device, to a mobile device and/or to a remote server via a telecommunications network. The microprocessor 702 may transmit the spectra via a wired port 706 and data communications interface, e.g., via USB chip on the board and a USB interface. The microprocessor 702 may transmit the spectra via the transmitter 704 that provides a wireless data communications interface, e.g., via Wi-Fi, Bluetooth and/or near-field communication (NFC).

The method 200 may include the following steps which are performed by the electronics: reading out and storing signals representing the one or more spectra (performed by the microprocessor 702); and transmitting the signals using a communications protocol (performed by the microprocessor 702 and the transmitter 704 for wireless communications) (step 214).

The spectra processed and stored by the microprocessor 702 may be sent to the data communication interfaces for outputting to the external computing device, e.g., a local computing device including a smart phone, or a remote server, via the wired connection or wireless connection. In some embodiments, the apparatus 100 may further include a display, and a processing result indicative of the property (or properties) of the plant product 108 may be converted into a visual form and presented to a user through the display. The data communication interfaces may include any data communication interface suitable for outputting the spectra to the external computing device, e.g., interfaces for enabling wired/wireless communication, such as USB, Wi-Fi, Bluetooth, and/or near-field communication (NFC).

The microprocessor 702 and the transmitter 704 may be from a commercially available microelectronic board, e.g., SparkFun ESP32 Thing board or an RF52832 chip by Nordic Semiconductors.

The spectrometer 118 may acquire at least one background spectrum while the light source 102 is not directing light onto the region 106 of the plant product 108. As shown in FIG. 2, the method 200 may include acquiring the background spectrum while the source light 104 is not being directed onto the region 106 of the plant product 108 (step 210). The electronics may be configured to generate one or more background-free spectra by removing the background spectrum from the one or more generated spectra indicative of the transmitted portion. The background-free spectra may be stored and/or transmitted by the microprocessor 702 and the communications protocol (step 214). Depending on the capabilities of the microprocessor 702, the background-free spectra may be stored and/or transmitted in addition to, or instead of, the generated spectra indicative of the transmitted portion.

Optimally, at step 210, the apparatus 100 is at a similar location relative to the region 106 as the apparatus 100 is when the light source 102 is illuminating the region 106 of the plant product 108, so substantially the same region 106 is used to generate the spectra and the background spectra: improved spacing of the region 106 and the apparatus 100 can be provided by the cup 400 and its spacer 404. At step 212, background-free spectra are generated by removing (e.g., subtracting) the background spectrum or spectra can from the one or more spectra indicative of the transmitted portion obtained while the source light 104 illuminates the region 106. This may remove or mitigate measurement of residual background light, such as sunlight, before the measurement spectra are stored and/or transmitted at step 214.

As shown in FIG. 5, the apparatus 100 can also include at least one power source for supplying electric power to the electronic components of the apparatus 100, i.e., the microprocessor 702, the transmitter 704, the light source 102 and/or the spectrometer 118. The power source may be a battery unit in the housing 126 (including a power battery, e.g., a LiPo cell battery, connected to the board via a plug 710), such that the apparatus 100 can be used for detection in the absence of external electrical power, and may therefore be portable. The battery unit may be rechargeable, e.g., via a charging port 706 such as a Micro-USB interface or pogo pins contact.

As shown in FIG. 5, the apparatus 100 can include a manual control 712, e.g., in the form of a button or activator, that can control the apparatus 100 to initiate a scan, i.e., start the method 200.

In some embodiments, the apparatus may be controlled from another device to initiate the scan, e.g., from the local computing device such as a smart phone through wired or wireless communication (e.g., USB, Wi-Fi, Bluetooth, and/or NFC).

Applications and Variations

According to at least some embodiments, provided herein is a portable, compact, light-weight apparatus 100 that can measure one or more properties of a plant product 108 based on fluorescence and reflection in a region 106 of the skin or surface of the plant product 108 under UV and VIS/NIR light illumination.

The apparatus 100 can be used to measure the properties of various types/varieties of fruits, vegetables and other plant products, e.g., apples, bananas, stone fruit including cherries, mango, avocadoes, etc.

By using the spectrometer 118, the apparatus 100 can detect emitted light 116 caused by fluorescence and/or diffuse reflection from the region 106 at a range of wavelengths, rather than at discrete wavelengths, and generate the one or more spectra based on these wavelengths. This means that the apparatus 100 can detect chlorophyll fluorescence as well as fluorescence and diffuse reflection from other pigments.

According to at least some embodiments, by utilising a plurality of VIS/NIR sources 504 and a plurality of UV light sources 502, the apparatus 100 may provide more uniform target illumination of region 106, compared to having only one VIS/NIR light source 504 and one UV light source 502.

Interpretation

The recitation of a particular numerical value or value range herein is understood to include or be a recitation of an approximate numerical value or value range, for instance, within +/−20%, +/−15%, +/−10%, +/−5%, +/−2.5%, +/−2%, +/−1%, +/−0.5%, or +/−0%. The term "substantially" can indicate a percentage greater than or equal to 90%, for instance, 92.5%, 95%, 97.5%, 99%, or 100%.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Many modifications will be apparent to those skilled in the art without departing from the scope of the present invention.

The invention claimed is:

1. A method for detecting at least one property of a plant product, the method including:
    directing source light including ultraviolet (UV) light at UV wavelengths from at least one UV light source and polarized visible and/or near-infrared (VIS/NIR) light at VIS/NIR wavelengths from at least one VIS/NIR light source onto a region of the plant product;
    blocking the polarized VIS/NIR light of the source light, and blocking polarized specular reflection from the region of the plant product caused at least by the polarized VIS/NIR light, from being transmitted to a visible and/or near-infrared (VIS/NIR) spectrometer; and
    transmitting a portion of emitted light caused by fluorescence and/or diffuse reflection from the region of the plant product to the visible and/or near-infrared (VIS/NIR) spectrometer;
    wherein the polarized VIS/NIR light and the polarized specular reflection are blocked by a spectrometer polarizer, wherein the transmitted portion is transmitted by the spectrometer polarizer, and wherein the spectrometer polarizer forms a crossed polarizer to the polarization of the polarized VIS/NIR light of the source light directed onto the plant product.

2. The method of claim 1, wherein the transmitted portion of the emitted light has an opposite polarization from the polarized VIS/NIR light of the source light.

3. The method of claim 1, wherein the emitted light is caused by the source light being directed onto the region.

4. The method of claim 1, wherein the fluorescence and/or diffuse reflection from the region is the pigment fluorescence and/or natural diffuse reflection from the region of the plant product.

5. The method of claim 1, wherein the method includes blocking the UV light of the source light and UV specular reflection from the region, and transmitting a portion of the emitted light with VIS/NIR wavelengths, and wherein the UV light and the UV specular reflection are blocked by a UV filter, and the transmitted portion is transmitted by the UV filter.

6. The method of claim 1, wherein the method includes:
generating one or more spectra that are indicative of the transmitted portion,
storing signals representing the one or more spectra, and transmitting the signals using a communications protocol; and/or
acquiring a background spectrum while the source light is not being directed onto the region of the plant product,
generating one or more background-free spectra by removing the background spectrum from the one or more spectra indicative of the transmitted portion,
storing signals representing the one or more background-free spectra, and
transmitting the signals using the communications protocol.

7. The method of claim 1, wherein the method includes housing the spectrometer in a protective housing.

8. An apparatus for detecting at least one property of a plant product, the apparatus including:
a light source including at least one UV light source and at least one VIS/NIR light source, the light source being configured to direct for directing source light including UV light at UV wavelengths from the at least one UV light source and polarized VIS/NIR light at VIS/NIR wavelengths from the at least one VIS/NIR light source onto a region of the plant product;
a spectrometer polarizer for blocking the polarized VIS/NIR light of the source light and polarized specular reflection from the region caused at least by the polarized VIS/NIR light from being transmitted to a visible and/or near-infrared (VIS/NIR) spectrometer, and for transmitting a portion of emitted light caused by fluorescence and diffuse reflection from the region, wherein the spectrometer polarizer forms a crossed polarizer to the polarization of the polarized VIS/NIR light of the source light directed onto the plant product; and
the visible-NIR (VIS/NIR) spectrometer for receiving the transmitted portion.

9. The apparatus of claim 8, including an UV filter for blocking the UV light of the source light and UV specular reflection from the region, and for transmitting the portion of the emitted light at VIS/IR wavelengths.

10. The apparatus of claim 8,
wherein the spectrometer generates one or more spectra that are indicative of the transmitted portion, and wherein the apparatus includes electronics configured for storing signals representing the one or more spectra indicative of the transmitted portion, and for transmitting the signals using a communications protocol; and/or
wherein the spectrometer acquires a background spectrum while the light source is not directing source light onto the region of the plant product, wherein the apparatus includes electronics configured for generating background-free spectra by removing the background spectrum from the one or more spectra indicative of the transmitted portion.

11. The apparatus of claim 8, wherein the apparatus includes a protective housing for protecting the spectrometer during use.

12. The apparatus of claim 8, wherein the spectrometer is arranged in substantially the same plane as the light source.

13. The apparatus of claim 8, wherein the at least one UV light source and the at least one VIS/NIR light source includes light emitting diodes (LEDs).

14. The apparatus of claim 13, wherein:
the at least one UV light source includes a plurality of UV light sources arranged in a geometrical arrangement or a sequence or a ring, and/or wherein the at least one VIS/NIR light source includes a plurality of VIS/NIR light sources arranged in a geometrical arrangement or a sequence or a ring;
the UV and VIS/NIR light sources are symmetrical about the spectrometer;
the plurality of UV light sources is arranged on opposite sides of the spectrometer;
the plurality of VIS/NIR light sources is arranged on opposite sides of the spectrometer; and/or
the UV light sources and the VIS/NIR light sources are combined into a plurality of arrays, with one array on either side of the spectrometer.

15. The apparatus of claim 8,
wherein the UV wavelengths include wavelengths between 360 and 405 nm;
wherein the VIS/NIR wavelengths include broadband wavelengths between 450 and 900 nm; and/or
wherein the light source includes a plurality of polarizers oriented in mutually the same direction.

16. The apparatus of claim 8,
wherein the apparatus further includes a cup to accommodate the plant product,
wherein the cup includes a non-linear circumference.

17. The apparatus of claim 16, wherein the cup substantially blocks the spectrometer from background light; and/or wherein the cup includes an internal plant product holder for holding the plant product at a selected distance from spectrometer, wherein the internal plant product holder includes two or more fins.

18. The apparatus of claim 8, wherein the apparatus includes a transmitter for transmitting the spectra and/or the calculated value via a wired or wireless data communications interface.

19. The method of claim 1, wherein the method includes: accommodating the plant product in cup with a non-linear circumference, and substantially blocking the spectrometer from background light with the cup.

20. The method of claim 19, wherein the method includes holding the plant product at a selected distance from spectrometer with an internal plant product holder includes.

* * * * *